(12) United States Patent
Saavedra Aguilar et al.

(10) Patent No.: US 11,278,026 B2
(45) Date of Patent: Mar. 22, 2022

(54) COMPOSITION BASED ON NORDIHYDROGUAIARETIC ACID

(71) Applicant: PROMOTORA TECNICA INDUSTRIAL, S.A. DE C.V., Mexico City (MX)

(72) Inventors: Mario Saavedra Aguilar, Mexico City (MX); Odon Vite Vallejo, Mexico City (MX)

(73) Assignee: PROMOTORA TECNICA INDUSTRIAL, S.A. DE C.V., Benito Juarez (MX)

(*) Notice: Subject to any disclaimer, the term of this patent is extended or adjusted under 35 U.S.C. 154(b) by 367 days.

(21) Appl. No.: 16/693,330

(22) Filed: Nov. 24, 2019

(65) Prior Publication Data

US 2020/0093126 A1 Mar. 26, 2020

Related U.S. Application Data

(62) Division of application No. 15/619,461, filed on Jun. 10, 2017, now abandoned.

(30) Foreign Application Priority Data

Feb. 17, 2017 (MX) .................... MX/a/2017/002227

(51) Int. Cl.
*A01N 31/16* (2006.01)
*A01N 65/08* (2009.01)
*A01N 65/22* (2009.01)
*A01N 65/00* (2009.01)
*A61K 31/047* (2006.01)
*A61K 47/10* (2017.01)

(52) U.S. Cl.
CPC .............. *A01N 31/16* (2013.01); *A01N 65/00* (2013.01); *A01N 65/08* (2013.01); *A01N 65/22* (2013.01); *A61K 31/047* (2013.01); *A61K 47/10* (2013.01)

(58) Field of Classification Search
None
See application file for complete search history.

(56) References Cited

U.S. PATENT DOCUMENTS

| | | |
|---|---|---|
| 4,562,298 A | 12/1985 | Parkhurst et al. |
| 6,372,239 B1 | 4/2002 | Wu et al. |
| 6,417,234 B1 | 7/2002 | Huang et al. |
| 6,608,108 B2 | 8/2003 | Huang et al. |
| 6,777,444 B2 | 8/2004 | Huang et al. |
| 8,318,815 B2 | 11/2012 | Huang et al. |
| 9,101,567 B2 | 8/2015 | Huang et al. |
| 9,149,526 B2 | 10/2015 | Huang et al. |
| 9,456,995 B2 | 10/2016 | Huang et al. |
| 2005/0123560 A1* | 6/2005 | Sinnott ................ A61K 36/185 424/195.18 |
| 2005/0244445 A1 | 11/2005 | Anderson |
| 2008/0096967 A1* | 4/2008 | Lopez .................... A61P 31/14 514/567 |
| 2008/0300225 A1 | 12/2008 | Marrone |
| 2015/0216181 A1 | 8/2015 | Hernandez Romero |

* cited by examiner

*Primary Examiner* — Michael Barker
(74) *Attorney, Agent, or Firm* — Craft Chu PLLC; Andrew W. Chu

(57) ABSTRACT

The pesticide and method of manufacturing includes one component extracted from an evergreen Bush "*Larrea tridentate*" the common name of which is Gobernadora, in which the main active ingredient is nordihydroguaiaretic acid(NDGA) 1,4-Bis(3,4-dihydroxyphenyl)-2,3-dimethylbutane, 4,4'-(2,3-Dimethyltetramethylene) dipyrocatechol. The composition of which is enriched with plant oils, emulsifiers and humidifiers, thus obtaining a product which can be easily used in crops with the help of sprinklers. Consequently, the action field of this procedure is within chemical compositions used to cultivate crops and fruit products.

1 Claim, No Drawings

COMPOSITION BASED ON NORDIHYDROGUAIARETIC ACID

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This invention refers to a pesticide which at least includes one component extracted from an evergreen Bush "Larrea tridentata" the common name of which is Gobernadora (in Spanish), in which the main active ingredient is nordihydroguaiaretic acid (NDGA) 1,4-Bis(3,4-dihydroxyphenyl)-2,3-dimethylbutane, 4,4'-(2,3-Dimethyltetramethylene) dipyrocatechol, the composition of which is enriched with plant oils, emulsifiers and humidifiers, thus obtaining a product which can be easily used in crops with different application methods.

This chemical composition is used as a pesticide to control fungal or bacterial diseases when cultivating vegetables, fruits, grains and cereals, industrial crops and other yearly and perennial crops without causing any inconvenience in the health of people or higher animals.

Its physical chemical characteristics have a high specificity on target organisms, minimum toxicity in mammals, low persistence in the environment and where the added ingredients may come, although not exclusively, from vegetable extracts.

Consequently, the action field of this procedure is within chemical compositions used to cultivate crops and fruit products.

2. Description of Related Art Including Information Disclosed Under 37 CFR 1.97 and 37 CFR 1.98

Nordihydroguaiaretic acid (NDGA) 1,4-Bis(3,4-dihydroxyphenyl)-2,3-dimethylbutane, 4,4'-(2,3-Dimethyltetramethylene) dipyrocatechol of developed formula:

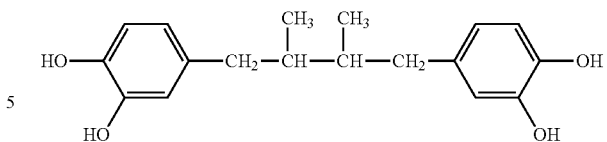

The Gobernadora (Larrea tridentata) common name so called in honor of Juan Antonio Hernandez Perez de Larrea, a Spanish clergyman born in 1730 and with the Latin designation tridentata which means three teeth, is widely used in rural areas against urinary conditions such as kidney stones to dissolve them by cooking the plant or the branches. It has also been discovered that the roots of this bush can produce chemicals that restrain the growth of roots. In addition, the nordihydroguaiaretic acid has antioxidant properties, and it is used to descale boilers.

The chemical composition of this invention includes a different use from that which was given to it before. It includes the extraction of the active ingredient of the Larrea tridentata, and where the nordihydroguaiaretic acid is mixed with plant oils, a humidifier and a dispersing agent. It has been observed that said composition is useful as a fungicide to eliminate anthracnose, and it can be used to handle certain fungal and bacterial diseases in perennial and yearly crops.

BRIEF SUMMARY OF THE INVENTION

One of the purposes of this invention is to have a formulation that allows its use when cultivating vegetables, fruits, grains and cereals, industrial crops and other yearly and perennial crops showing fungal or bacterial diseases such as anthracnose, mildew, bacterial spots, bacterial spots on leaves, root and neck rot, blight, etc. by means of an application method thus improving the health of said crops.

Its goal is to have a useful and practical chemical preparation which can be safely used, and to develop a composition based on botanical active principles to obtain a mixture of secondary metabolites chemically different among themselves thus preventing the possible resistance development in pests.

Likewise, a characteristic of this invention is the fact that it can be prepared in bulk and under the necessary conditions to be industrialized complying with strict specifications and providing an optimal yield while assuring its efficiency.

BRIEF DESCRIPTION OF THE SEVERAL VIEWS OF THE DRAWINGS

None.

DETAILED DESCRIPTION OF THE INVENTION

A formula (chemical composition) is described beginning with harvesting Larrea tridentata leaves, without the branches and roots, being careful of not damaging the leaves when they are cut, and placing said leaves in sacks.

Said plant material must be analyzed in order to determine the percentage of nordihydroguaiaretic acid present to make sure the extract will contain the minimum necessary amount of the metabolite.

The drying and extracting process must be carefully watched not to exceed the allowed maximum temperature, to prevent the degradation of nordihydroguaiaretic acid which will affect the quality of the extract.

After the previous step is finished, the product is discharged and filtered to remove the leaves from the liquid.

With this raw material a composition is prepared that has pesticide properties to control fungal and bacterial diseases such as anthracnose, mildew, bacterial spots, bacterial spots on leaves, root and neck rot, blight, etc. in vegetable and fruit crops, grains and cereals and in industrial crops and other yearly and perennial crops.

The standard formula (chemical composition) of this invention is described herein below, mentioning the percentage of the components that can be present without these affecting the biological activity of said formula. The proportion may vary depending on the purity of its ingredients, yet keeping the characteristics of the specific modality. The formula is expressed as follows:

Formula expressed in percentage

| | |
|---|---|
| *Larrea tridentata* extract (Nordihydroguaiaretic Acid) | 50-95% |
| Botanical extract or plant oil | 1-15% |
| Adjuvants | 1-5% |
| Vehicle | 5-50% |

The botanical extract or the plant oils come from plants such as *Piper nigrum, Origanum vulgare, Allium* sp. *Equisetum* sp, *Thymus* sp, *Schinus molle, Chenopodium* sp y *Ruta* sp.

Adjuvants used are ascorbic acid and sorbitan polyoxietilene monolaurate or ethoxilated castor oil (by themselves or in a 1:1 mixture) which act as dispersant agents multiplying the beneficial effects of adherence, compatibility, pH correction, thus reducing evaporation and penetration.

The vehicle is a mixture of ethanol—water used as an extraction agent for the extracts and as solvent.

In order to develop the chemical preparation, as a first step the extracts were evaluated by themselves and in combination, and selecting those in which growth of phytopatogenic agent inhibition was partial or total. The extracts themselves and the selected mixtures were chemically prepared with the adjuvants and the vehicles to obtain the chemical preparation same which later were submitted to an assay.

Below, the most relevant results in the aspect of fungi and phytopatogenic bacteria inhibition are shown.

d) Let the product cool until room temperature is reached and filter to completely eliminate any vegetable residues.
e) The obtained product is characterized by the nordihydroguaiaretic acid content through chromatographic techniques.
f) Perform the concentration adjustment by adding the vehicle and finally add the preservative. If necessary the pH of the product is again adjusted to 5.0 to 6.0

With the extract obtained the above description of the process serial dilutions in 0.01, 0.1, 0.5, 1.0, y 2.0% were prepared and submitted to a biological effectiveness essay using different species of microorganisms. The study was carried out with the optimal growth conditions recorded in technical literature. After 5 days in the study, the effect caused by the different extract concentrations of each assessed species was determined.

Table 1 clearly shows the results of its effectiveness. It can be seen that 0.01 and 0.1% concentrations do not have any inhibitory effect on the assessed species, yet as of a 0.5% concentration it is observed that there is an effect of inhibition in the growth and in the development of the assessed organisms.

TABLE 1

Assessment of *Larrea* extract against three phytopatogenic fungi isolations in vitro

| | *Fusarium* sp | *Alternaria* sp | *Colletotrichum* sp |
|---|---|---|---|
| Extract 0.01% | no inhibition | no inhibition | no inhibition |
| Extract 0.1% | no inhibition | no inhibition | no inhibition |
| Extract 0.5% | no inhibition | Inhibition | no inhibition |
| Extract 1.0% | no inhibition | Inhibition | Inhibition |
| Extract 2.0% | Inhibition | Inhibition | Inhibition |

Based on the results shown in Table 1, 1.0% extract concentration was evaluated adding different botanical extracts same that would complement its biological activity. In Table 2 the indicated mixtures are described in a 10 mL/L dosage under the same environmental conditions in the first assessment.

TABLE 2

Assessment of the *Larrea* extract combined with botanical extracts in a hydroalcoholic stage vs phytophatogenic fungi isolations in vitro

| | *Fusarium* sp | *Alternaria* sp | *Colletotrichum* sp |
|---|---|---|---|
| *Larrea* extract + *Thymus* | Partial inhibition | Partial inhibition | Partial inhibition |
| *Larrea* extract + *Ruta* | Complete inhibition | Complete inhibition | Partial inhibition |
| *Larrea* extract + *Allium* | Complete inhibition | Complete inhibition | Complete inhibition |
| *Larrea* extract + *Piper* | Partial inhibition | Complete inhibition | Partial inhibition |
| *Larrea* extract + *Equisetum* | Complete inhibition | Partial inhibition | Complete inhibition |

EXAMPLE 1

The primary extract of *Larrea tridentata* was obtained with the following procedure:

a) Weigh 500 to 750 g of the grinded vegetal material and sifted with a #40 mesh.
b) Place the vegetal material in a container having a temperature and stirring system.
c) Add the alcohol and monolaurate mixture, heat to a 50 to 70° temperature and allow the material to humidify for 2 to 4 hours. Check that pH remains at 5.5. Keep the temperature and stirring conditions during at least 8 more hours.

According to this evaluation it was observed that the biological activity of the mixture of extracts has a clear effect on the development and on the growth of fungi because in all of the cases there was the presence of the inhibitory effect. The most complete was that in which there was no fungi growth on the culture medium used.

In Table 4 the extracts were evaluated again, but with three different species of phytopatogenic bacteria in order to observe if there was also an effect as a bactericide. The essay was carried out with a 10 mL/L dosage and with an incubation period of 36 hours at 30° C.,

TABLE 4

Assessment of the *Larrea* extract combined with botanical extracts in a hydroalcoholic stage vs phytopatogenic bacteria.

| | *Streptomyces* sp | *Xhantomonas* sp | *Clavibactr* sp |
|---|---|---|---|
| *Larrea* extract + *Thymus* | Partial inhibition | Complete inhibition | Partial inhibition |
| *Larrea* extract + *Ruta* | Complete inhibition | Complete inhibition | Partial inhibition |
| *Larrea* extract + *Allium* | Complete inhibition | Complete inhibition | Complete inhibition |
| *Larrea* extract + *Piper* | Complete inhibition | Complete inhibition | Complete inhibition |
| *Larrea* extract + *Equisetum* | Complete inhibition | Complete inhibition | Complete inhibition |

In this case sensitivity of bacteria to the mixture of extracts was higher because the inhibition is complete in almost all of the cases. This is seen by the fact that there was no growth of colonies during the assessment period.

Based on the results above, chemical preparations using the evaluated extracts (variable proportions) were prepared and the adjutants described in the mentioned percentages, in the percentage composition were added. The preparations obtained were assessed in vitro against six phytopatogenic agents with a dosage of 10 ml/L of the chemical preparation per liter of water under the same environmental conditions as the essays above. The effects of the different preparations are described in Table 5.

TABLE 5

Assessment of *Larrea Tridentata* Extract combined with botanical extracts and coadjutans vs phytopatogenic organisms.

| | *Fusarium* sp | *Sclerotium* sp | *Colletotichum* sp | *Streptomyces* sp | *Xhantomonas* sp | *Clavibacter* sp |
|---|---|---|---|---|---|---|
| Preparation 1 | Partial | Complete | Complete | Complete | Complete | Partial |
| Preparation 2 | Complete | Complete | Partial | Complete | Partial | Complete |
| Preparation 3 | Partial | Complete | Complete | Complete | Complete | Complete |
| Preparation 4 | Complete | Partial | Complete | Partial | Partial | Partial |
| Preparation 5 | Partial | Partial | Complete | Complete | Complete | Partial |

According to the results of these essays, each one of the preparations evaluated is able to inhibit the growth and the development of certain phytopatogenic organisms, due to the fact that its activity can be described as a fungicide and a bactericide.

Best Way to Put the Invention to Practice

According to the data in the tables above, the precise combination of extracts, adjuvants and vehicles result in a preparation the fungicide and bactericide action of which allows controlling phytopatogenic agents of agricultural importance. The product that was developed is constituted by natural extracts that do not have a negative impact on the environment.

We claim:

1. A chemical composition, comprising:
   a *Larrea tridentate* extract at 50-95 wt %, being comprised of nordihydroguaiaretic acid;
   a plant compound selected from the group consisting of a botanic extract and plant oil at 1-15 wt %;
   an adjuvant at 1-5 wt %; and
   a vehicle at 5-50 wt %,
   wherein said plant compound is selected from the group consisting of *Piper nigrum, Origanum vulgare, Allium* sp, *Equisetum* sp, *Thymus* sp, *Schinus molle, Chenopodium* sp and *Ruta* sp,
   wherein said adjuvant is selected from the group consisting of ascorbic acid, sorbitan polyoxyethylene monolaurate and ethoxylated castor oil, said adjuvant being a dispersant, and
   wherein said vehicle is comprised of ethanol and water.

* * * * *